US007763767B2

(12) United States Patent
Pilliod et al.

(10) Patent No.: US 7,763,767 B2
(45) Date of Patent: Jul. 27, 2010

(54) ADSORPTION PROCESS WITH ON-LINE ADSORBENT REMOVAL

(75) Inventors: Dana Lynn Pilliod, League City, TX (US); Katy Conley Randall, Seabrook, TX (US); Eric Martin Harding, Baytown, TX (US)

(73) Assignee: ExxonMobil Chemicals Patents Inc., Houston, TX (US)

( * ) Notice: Subject to any disclaimer, the term of this patent is extended or adjusted under 35 U.S.C. 154(b) by 1453 days.

(21) Appl. No.: 11/122,312

(22) Filed: May 4, 2005

(65) Prior Publication Data
US 2006/0252972 A1 Nov. 9, 2006

(51) Int. Cl.
C07C 7/12 (2006.01)

(52) U.S. Cl. .................. 585/828; 585/820; 585/826; 585/827

(58) Field of Classification Search .............. None
See application file for complete search history.

(56) References Cited

U.S. PATENT DOCUMENTS

| | | | |
|---|---|---|---|
| 2,631,727 A * | 3/1953 | Cichelli | 208/310 R |
| 2,765,282 A | 10/1956 | Elliott | |
| 2,859,170 A | 11/1958 | Dickens et al. | |
| 2,921,014 A | 1/1960 | Marshall | |
| 3,161,582 A | 12/1964 | Wickham | |
| 3,424,672 A | 1/1969 | Mitchell | |
| 3,448,037 A | 6/1969 | Bunn, Jr. et al. | |
| 3,686,342 A | 8/1972 | Neuzil | |
| 3,761,533 A * | 9/1973 | Otani et al. | 585/802 |
| 3,838,038 A | 9/1974 | Greenwood et al. | |
| 3,838,039 A | 9/1974 | Vesley et al. | |
| 4,224,147 A | 9/1980 | Traut | |
| 4,416,798 A | 11/1983 | Hager et al. | |
| 4,462,904 A | 7/1984 | Hager et al. | |
| 4,940,830 A | 7/1990 | Zinnen et al. | |
| 5,076,908 A | 12/1991 | Stangeland et al. | |
| 5,258,563 A | 11/1993 | Gosling et al. | |
| 5,310,477 A | 5/1994 | Lomas | |
| 5,405,586 A | 4/1995 | Koves | |
| 5,589,057 A | 12/1996 | Trimble et al. | |
| 5,599,440 A | 2/1997 | Stangeland et al. | |
| 5,603,904 A | 2/1997 | Bachtel et al. | |
| 6,338,792 B1 | 1/2002 | Laricchia | |
| 6,402,958 B1 | 6/2002 | Moran | |
| 2002/0164278 A1 | 11/2002 | Vetter et al. | |

FOREIGN PATENT DOCUMENTS

| | | |
|---|---|---|
| DE | 3321605 A | 12/1984 |
| DE | 3541414 | 5/1987 |
| DE | 3321605 C | 9/1989 |
| DE | 4142806 A | 6/1993 |
| GB | 2057910 | 4/1981 |
| GB | 2201964 | 9/1988 |
| WO | WO 89/07487 | 8/1989 |
| WO | WO99/38823 | 8/1999 |
| WO | 2006/118740 | 11/2006 |

OTHER PUBLICATIONS

"Handbook of Petroleum Refining Processes", R.A. Myers, McGraw-Hill, New York, 1986; pp. 8-79-8-99.
"Atlas of Zeolite Structure Types", Eds. W. H. Meier, D. H. Olson and Ch. Baerlocher, Elsevier, Fourth Edition, 1996.
"Fluid Flow Through Packed Columns", Chem. Eng. Prog. 48: 89-94, Feb. 1952, S. Ergun.
"Perry's Chemical Engineers' Handbook", Eds. R. H. Perry, D. W. Green and J. O. Maloney, McGraw-Hill Book Company, Sixth Edition, 1984.
"Zeolite Molecular Sieve", Donald W. Breck, Robert E. Krieger Publishing Company, Inc., 1984, pp. 4-24-4-29, and pp. 20-58-20-61.
"Catalyst Manufacture", Alvin B. Stiles, Theodore A. Koch, Marcel Dekker, Inc., 2nd Edition, 1995, pp. 85-95.
Abstract of DE 4142806, 1993.
Abstract of DE 3321605 A, 1984.
Abstract of DE 3321605 C, 1989.

* cited by examiner

Primary Examiner—Tam M Nguyen
(74) Attorney, Agent, or Firm—Andrew B. Griffis

(57) ABSTRACT

This invention relates to a process for conversion of hydrocarbon feedstock, comprising the steps of (A) feeding the hydrocarbon feedstock to an adsorption unit; (B) adsorbing the hydrocarbon feedstock in the adsorption unit with a solid particulate adsorbent useful for adsorbing at least one component from the hydrocarbon feedstock under adsorption conditions; (C) withdrawing the adsorbed feedstock from the adsorption unit; (D) desorbing the component(s) from the solid particulate adsorbent; and (E) removing, under the adsorption conditions for a fractional time of step (B), at least a portion of said adsorbent while the feedstock is being fed to the adsorption unit.

29 Claims, No Drawings

ADSORPTION PROCESS WITH ON-LINE ADSORBENT REMOVAL

FIELD OF THE INVENTION

The present invention relates to a process for hydrocarbon conversion by contacting a feedstock suitable for hydrocarbon conversion under conversion conditions with a solid particulate material and removing at least a portion of the solid particulate material under conversion conditions during at least a portion of the hydrocarbon conversion process.

BACKGROUND OF THE INVENTION

Hydrocarbons are valuable commercial products. For example, ethylene, propylene, benzene, toluene, and para-xylene are valuable commercial products useful in the production of polymers, gasoline, and other chemicals.

Olefins and aromatic compounds can be formed by catalytic and separation processes. For example, aromatic compounds can be formed by converting non-aromatic compounds to aromatic compounds, e.g., dehydrocyclooligomerization, reforming, and catalytic cracking. Also, less valuable aromatic compounds can be converted into more valuable aromatic compounds. Examples of such processes include the methylation of toluene to form xylenes, the disproportionation of toluene to form xylenes and benzene, and the isomerization of xylene feedstock to produce a product enriched in para-xylene. Olefins can be produced by catalytic cracking of paraffins, e.g., a fluidized catalytic cracking process. High value purified olefins and aromatics can be manufactured by separation processes such as selective adsorption processes. Examples of such processes include Parex™, which separates para-xylene from mixed $C_8$ aromatic isomers, Olex™, which separates olefins from paraffins in a wide boiling hydrocarbon mixture, and Ebex™, which separates ethylbenzene from mixed $C_8$ aromatic isomers. These processes typically use at least one solid particulate material, such as a catalyst and/or a solid adsorbent.

Many commercial catalytic and adsorption processes suffer problems such as, deactivation, coking, and overall attrition resulting in high pressure-drop across a catalyst bed or adsorbent bed. These problems can degrade or otherwise impair the performance of the process such as conversion, selectivity, and productivity (including overall product recovery). In some instances these problems can require alteration of operation conditions of the process such as temperature, pressure, and weight hour space velocity (WHSV). One solution to the problems for catalytic processes is to compensate for activity lost due to the catalyst deactivation by increasing reaction temperature. However, increasing the reaction temperature increases energy consumption. Furthermore, the reaction temperature is limited by the metallurgy of the reactor material. Another solution to these problems for catalytic and/or adsorption processes is regeneration or rejuvenation of the catalyst or adsorbent, which normally requires unit shut down for a certain period of time. In some cases, fresh catalyst or adsorbent will have to be reloaded to replace the spent catalyst or adsorbent.

Typical reactors and adsorption chambers have a designed pressure-drop depending on the applications. The pressure-drop across the catalyst bed or the adsorbent bed typically increases over time after the catalyst bed or the adsorbent bed is brought on-line. Extra pressure-drop across the catalyst bed or the adsorbent bed is an operational problem in commercial hydrocarbon conversion processes. While not intending to be limited to any theory, we believe that the extra pressure-drop across the catalyst bed or the adsorbent bed results from the formation of fines (including attrition and/or crushing of adsorbent and/or catalyst), coke formation, deposition of impurities and/or solids in the feedstock(s) on the catalyst or adsorbent, and movement of the catalyst or adsorbent in the reactor or the adsorption vessel. One solution to this problem is to increase pressure head for the feedstream(s), but increasing the pressure head increases energy consumption. Furthermore, the maximum pressure head is limited by the mechanical design of associated equipment and the process conditions of the upstream and/or the downstream processes. In some cases, the catalyst and/or adsorbent have to be changed-out with fresh or regenerated catalyst and/or adsorbent, which requires a costly unit shutdown.

U.S. Pat. No. 3,838,038 (Greenwood et al.) and U.S. Pat. No. 3,838,039 (Vesley et al.) disclose a process for hydrocarbon processing in conjunction with continuous catalyst regeneration. The process utilizes a moving bed reaction zone and a continuous regeneration zone, which causes the burning of carbonaceous material off of a catalyst that has been withdrawn from the reaction zone. The regenerated catalyst is continuously supplied back to the moving bed reaction zone.

U.S. Pat. No. 5,589,057 (Trimble et al.), U.S. Pat. No. 5,599,440 (Stangeland et al.), U.S. Pat. No. 5,603,904 (Bachtel et al.), and U.S. Pat. No. 5,076,908 (Stangeland et al.) disclose a reactor having a cone or screen at the bottom thereof to support the catalyst. The catalyst stream enters at the top of the reaction counter-current to the flow of the gas and the hydrocarbon, which enters at the bottom. As the feed moves up through the catalyst, these particles become heavier and move downward through the reactor toward the entering feed stream and are finally withdrawn at the bottom of the reactor.

U.S. Pat. No. 2,921,014 (Marshall), U.S. Pat. No. 3,161,582 (Wickham), U.S. Pat. No. 3,424,672 (Mitchell), U.S. Pat. No. 3,448,037 (Bunn, Jr. et al.), and U.S. Pat. No. 5,310,477 (Lomas) disclose catalytic cracking of hydrocarbon feed in a fluidized bed with smooth and stable catalyst circulation and regeneration. The spent catalyst is constantly removed from the reaction zone, regenerated in the regenerator and resupplied back to the reaction zone.

The present invention relates to a hydrocarbon conversion process comprising a step of removing, under the conversion conditions without interruption of on-going process, at least a portion of the solid particulate material in the reaction and/or separation zone.

SUMMARY OF THE INVENTION

In one embodiment, the present invention relates to a process for conversion of a hydrocarbon feedstock, comprising the steps of:

A) feeding the hydrocarbon feedstock to an adsorption unit;

B) adsorbing the hydrocarbon feedstock in the adsorption unit with a solid particulate adsorbent useful for adsorbing at least one component from the hydrocarbon feedstock under adsorption conditions;

C) withdrawing adsorbed hydrocarbon feedstock from the adsorption unit;

D) desorbing at least one adsorbed component from the solid particulate adsorbent;

E) removing, under the adsorption conditions, at least a portion of the solid particulate adsorbent while the hydrocarbon feedstock is being fed to the adsorption unit, wherein the portion is more than 0.1 wt. % of the solid particulate adsorbent in the adsorption unit and wherein the adsorbent removal occurs during a fraction of the time of step (B), the fraction being less than about 95% of the time of step (B); and F) redistributing the remaining solid particulate adsorbent in the adsorption unit.

In another embodiment, the present invention relates a process for selective para-xylene adsorption comprising the steps of:

A) feeding a feedstock containing para-xylene to an adsorption unit;
B) adsorbing the feedstock in the adsorption unit with a solid particulate adsorbent useful for adsorbing at least one component from the feedstock under adsorption conditions;
C) withdrawing adsorbed feedstock from the adsorption unit;
D) desorbing the adsorbed component from the solid particulate adsorbent; and
E) removing, under the adsorption conditions, at least a portion of the solid particulate adsorbent while the feedstock is being fed to the adsorption unit, wherein the portion is more than 0.1 wt. % of the solid particulate adsorbent in the adsorption unit and wherein the solid particulate adsorbent removal occurs during a fraction of the time of step (B), the fraction being less than about 95% of the time of step (B).

In another embodiment, the present invention relates a process for selective para-xylene adsorption comprising the steps of:

A) feeding a feedstock containing para-xylene to an adsorption unit;
B) adsorbing the feedstock in the adsorption unit with a solid particulate adsorbent useful for adsorbing at least one component from the feedstock under adsorption conditions;
C) withdrawing adsorbed feedstock from the adsorption unit;
D) desorbing the adsorbed component from the solid particulate adsorbent;
E) monitoring a pressure-drop across at least a portion of the adsorption unit;
F) removing, under the adsorption conditions, at least a portion of the solid particulate adsorbent while the feedstock is being fed to the adsorption unit, the removing step is initiated when the pressure-drop is above a pre-set pressure-drop upper limit, and the removing step is continued at least until the pressure-drop is below the pre-set pressure-drop upper limit; and
G) redistributing the remaining solid particulate adsorbent in the adsorption unit, wherein the portion is more than 0.1 wt. % of the solid particulate adsorbent in the adsorption unit, wherein the solid particulate adsorbent removal occurs during a fraction of the time of step (B), the fraction being less than about 95% of the time of step (B), wherein the selective para-xylene adsorption is Parex™, and wherein the redistributing step is performed less than two weeks after the completion of the removal step.

DETAILED DESCRIPTION OF THE INVENTION

The term "hydrocarbon conversion", as used herein, shall mean the production of hydrocarbons by the conversion of a hydrocarbon feedstock. The term "hydrocarbon conversion", as used herein, shall also include the conversion of feedstock comprising hydrocarbon compounds to a product comprising other hydrocarbon compounds, which differ from said feedstock in composition, concentration of at least one component, or both composition and concentration of at least one component. The term "hydrocarbon conversion", as used herein, further includes the separation of hydrocarbons, e.g., adsorptive separation of alkyl substituted benzenes such as xylenes, for the purpose of separating various isomers of the hydrocarbons, e.g., separation of para-xylene from orthoxylene and meta-xylene.

The hydrocarbon conversion processes are used for processing hydrocarbon feedstocks. Hydrocarbon feedstocks contain carbon compounds and can be from many different sources, such as virgin petroleum fractions, recycle petroleum fractions, and tar sand oil. More broadly, hydrocarbon feedstocks can be any carbon containing fluid susceptible to catalytic reactions or adsorption. Depending on the type of processing the hydrocarbon feed is to undergo, the feed can contain metal or can be free of metals. Also, the feed can have high or low nitrogen or sulfur impurities. In an embodiment of the present invention, the feedstock comprises hydrocarbons having 1-20 carbons, oxygenates, or any combination thereof. In yet another embodiment, the feedstock comprises aromatics having 1-15 carbons, preferably para-xylene. In another embodiment, the feedstock further optionally comprises hydrogen.

Examples of hydrocarbon compound conversion processes that find application in the process of the present invention include, as non-limiting examples, the following:

A. The catalytic cracking of a naphtha feedstock to produce light olefins. Typical reaction conditions include temperatures from about 500° C. to about 750° C., pressures of about 10 kilo-Pascal absolute (hereinafter kPa-a) or 100 kPa-a, generally ranging up to about 1200 kPa-a and residence time (volume of the catalyst/feed volume rate) from about 10 milliseconds to about 10 seconds;

B. The catalytic cracking of high molecular weight hydrocarbons to lower weight hydrocarbons. Typical reaction conditions for catalytic cracking include temperatures of from about 400° C. to about 900° C., pressures of from about 10 kPa-a to about 3040 kPa-a, and weight hourly space velocities of from about 0.1 to about 100 $hr^{-1}$;

C. The transalkylation of aromatic hydrocarbons in the presence of polyalkylaromatic hydrocarbons. Typical reaction conditions include a temperature of from about 100° C. to about 500° C., a pressure of from about 100 to about 20000 kPa-a, a weight hourly space velocity of from about 1 to about 100 $hr^{-1}$ and an aromatic hydrocarbon/polyalkylaromatic hydrocarbon mole ratio of from about 0.5/1 to about 16/1;

D. The isomerization of aromatic (e.g., xylene) feedstock components. Typical reaction conditions include a temperature of from about 230° C. to about 510° C., a pressure of from about 50 to about 5000 kPa-a, a weight hourly space velocity of from about 0.1 to about 200 $hr^{-1}$ and a hydrogen/hydrocarbon mole ratio of from about 0 to about 100;

E. The dewaxing of hydrocarbons by selectively removing straight chain paraffins. The reaction conditions are dependent in large measure on the feed used and upon the desired pour point. Typical reaction conditions include a temperature between about 200° C. and 450° C., a pressure up to 20000 kPa-a and a liquid hourly space velocity from 0.1 to 20 $h^{-1}$;

F. The alkylation of aromatic hydrocarbons, e.g., benzene and alkylbenzenes, in the presence of an alkylating agent, e.g., olefins, formaldehyde, alkyl halides and alcohols having 1 to about 20 carbon atoms. Typical reaction conditions include a temperature of from about 100° C. to about 500° C., a pressure of from about 100 to about 20000 kPa-a, a weight hourly space velocity of from about 1 to about 200 hr$^{-1}$ and an aromatic hydrocarbon/alkylating agent mole ratio of from about 1/1 to about 20/1;

G. The alkylation of aromatic hydrocarbons with light olefins to provide short chain alkyl aromatic compounds, e.g., the alkylation of benzene with propylene to provide cumene. Typical reaction conditions include a temperature of from about 10° C. to about 200° C., a pressure of from about 100 to about 3000 kPa-a, and an aromatic hydrocarbon weight hourly space velocity (WHSV) of from 1 to about 50 hr$^{-1}$;

H. The hydrocracking of heavy petroleum feedstocks, cyclic stocks, and other hydrocrack charge stocks. The zeolite catalyst system will contain an effective amount of at least one hydrogenation component of the type employed in hydrocracking catalysts. The reaction conditions depend on the feedstock composition. Preferred reaction conditions include temperatures from about 100° C. to about 900° C., a pressure of from about 100 to about 7000 kPa-a, and a WHSV from about 0.1 to about 200 hr$^{-1}$;

I. The alkylation of a reformate containing substantial quantities of benzene and toluene with fuel gas containing short chain olefins (e.g., ethylene and propylene) to produce mono- and dialkylates. Preferred reaction conditions include temperatures from about 100° C. to about 300° C., a pressure of from about 800 to about 6000 kPa-a, a WHSV based on olefin from about 0.1 to about 10 hr$^{-1}$, a WHSV based on reformate of from about 1 to about 20 hr$^{-1}$;

J. The alkylation of phenols with olefins or equivalent alcohols to provide long chain alkyl phenols. Typical reaction conditions include temperatures from about 100° C. to about 250° C., pressures from about 100 to 3000 kPa-a and total WHSV of from about 2 to about 10 hr$^{-1}$;

K. The conversion of light paraffins (e.g., methane, ethane, propane, $C_1$-$C_5$ paraffins, and $C_1$ to $C_5$ olefins) to olefins and/or aromatics. Typical reaction conditions include temperatures from about 400 to about 950° C. and pressures from about 100 to about 1500 kPa-a. Processes for preparing aromatic compounds from light paraffins are described in U.S. Pat. No. 5,258,563, which is hereby incorporated by reference;

L. The conversion of light olefins to gasoline, distillate and lube range hydrocarbons. Typical reaction conditions include temperatures of from about 155° C. to about 400° C. and a pressure of from about 800 to about 15000 kPa-a;

M. Two-stage hydrocracking for upgrading hydrocarbon streams having initial boiling points above about 200° C. to premium distillate and gasoline boiling range products or as feed to further fuels or chemicals. In a first stage, the catalyst comprising one or more catalytically active substances, e.g., a Group VIII metal, and the effluent from the first stage would be reacted in a second stage using a second catalyst comprising one or more catalytically active substances, e.g., a Group VIII metal, as the catalyst. Typical reaction conditions include temperatures from about 300° C. to about 500° C., a pressure from about 2000 to about 20000 kPa-a, and a liquid hourly space velocity (LHSV) of from about 0.1 to 10 h$^{-1}$;

N. A combination hydrocracking/dewaxing process in the presence of the zeolite catalyst comprising a hydrogenation component and a zeolite such as zeolite Beta. Typical reaction conditions include temperatures from about 350° C. to about 400° C., pressures from about 5000 to about 10000 kPa-a, a liquid hourly space velocity (LHSV) of from about 0.4 to about 0.6 h$^{-1}$;

O. The reaction of alcohols with olefins to produce mixed ethers, e.g., the reaction of methanol with isobutene and/or isopentene to provide methyl-t-butyl ether (MTBE) and/or t-amyl methyl ether (TAME). Typical conversion conditions include temperatures from about 20° C. to about 200° C., pressures from 100 to about 20000 kPa-a, WHSV based on olefin feedstock from about 0.1 to about 200 hr$^{-1}$ and an alcohol to olefin molar feed ratio from about 0.1/1 to about 5/1;

P. The disproportionation of aromatics, e.g., the disproportionation of toluene to make benzene and para-xylene. Typical reaction conditions include a temperature of from about 200° C. to about 760° C., a pressure of from about 100 to about 6000 kPa-a, and a WHSV of from about 0.1 to about 30 hr$^{-1}$;

Q. The conversion of naphtha (e.g., $C_6$-$C_{10}$) and similar mixtures to highly aromatic mixtures. Thus, normal and slightly branched chained hydrocarbons, preferably having a boiling range above about 40° C., and less than about 200° C., can be converted to products having a substantial higher octane aromatics content by contacting the hydrocarbon feed with a catalyst at a temperature in the range of from about 400° C. to 600° C., preferably 480° C. to 550° C. at pressures ranging from 100 to 4000 kPa-a, and liquid hourly space velocities (LHSV) ranging from 0.1 to 15 h$^{-1}$;

R. The adsorption of alkyl aromatic compounds for the purpose of separating various isomers of the compounds;

S. The conversion of oxygenates, e.g., alcohols, such as methanol, or ethers, such as dimethylether, or mixtures thereof to hydrocarbons including olefins and aromatics under conversion conditions including a temperature of from about 275° C. to about 600° C., a pressure of from about 50 to about 5000 kPa-a and a liquid hourly space velocity of from about 0.1 to about 100 h$^{-1}$;

T. The oligomerization of straight and branched chain olefins having from about 2 to about 5 carbon atoms. The oligomers, the products of the process, are medium to heavy olefins, which are useful for both fuels, i.e., gasoline or a gasoline blending stock, and chemicals. The oligomerization process is generally carried out by contacting the olefin feedstock in a gaseous state phase with a zeolite catalyst at a temperature in the range of from about 250° C. to about 800° C., a LHSV of from about 0.2 to about 50 h$^{-1}$ and a hydrocarbon partial pressure of from about 10 to about 5000 kPa-a. Temperatures below about 250° C. may be used to oligomerize the feedstock when the feedstock is in the liquid phase when contacting the zeolite catalyst. Thus, when the olefin feedstock contacts the catalyst in the liquid phase, temperatures of from about 10° C. to about 250° C. may be used;

U. The conversion of $C_2$ unsaturated hydrocarbons (ethylene and/or acetylene) to aliphatic $C_6$-$C_{12}$ aldehydes and converting said aldehydes to the corresponding $C_6$-$C_{12}$ alcohols, acids, or esters;

V. The dehydrogenation of cycloaliphatics having 6 member rings. Typical reaction conditions include a temperature of from about 300° C. to about 700° C., a pressure of from about 10 to about 1000 kPa-a, a weight hourly space velocity of from about 0.1 to about 20 hr$^{-1}$; and W. The dehydration of alcohols to form aromatics, such as the dehydration of cyclohexane-triol to form benzene.

In general, catalytic conversion conditions include a temperature of from about 50° C. to about 950° C., a pressure of from about 10 to about 20000 kPa-a, and a weight hourly space velocity of from about 0.08 to about 2,000 hr$^{-1}$.

The term "reactor" as used herein, includes a catalytic reactor, a separation unit, or any combination thereof. A catalytic reactor includes a reactor comprising at least one reaction zone, a multi-stage reactor comprising a plurality of reaction stages or reactor vessels, a multi-bed reactor comprising a plurality of reaction beds, or any combination thereof. A separation unit includes an adsorption unit comprising at least one adsorbent bed, a multi-stage adsorption unit comprising a plurality of adsorption stages or adsorption vessels, a multi-bed adsorption unit comprising a plurality of adsorption beds, or any combination thereof. The conversion of hydrocarbon feeds can take place in any convenient mode, for example, in fluidized bed, moving bed, swing bed, simulated moving bed, or fixed bed reactors depending on the type of process desired. These types of reactor and their designs are described in "Perry's Chemical Engineers' Handbook", Eds. R. H. Perry, D. W. Green and J. O. Maloney, McGraw-Hill Book Company, Sixth Edition, 1984, which is hereby incorporated by reference.

In one embodiment of the present invention, the reactor and/or adsorption unit comprises a fixed bed unit, a fluidized bed unit, a rising-bed unit, a moving bed unit, or any combination thereof. In one embodiment of the present invention, the reactor and/or adsorption unit comprises at least one vessel and/or at least one bed.

The term "pressure-drop" as used herein, means the pressure difference across a designated unit or portion thereof, e.g., the pressure difference across the reactor and/or adsorption vessel(s), the reactor and/or adsorption bed(s), or the reactor and/or adsorption trays(s). The pressure-drop may be measured in any convenient way, e.g., by installing at least one pressure measuring device, such as a pressure gauge, at both inlet and outlet of the unit or portion thereof. The pressure-drop may be calculated by subtracting the pressure reading of an upstream pressure measuring device from the pressure reading of a downstream pressure measuring device. The pressure-drop may be also measured by indirect means. For example, in a two-bed adsorption unit, the pressure-drop of the first bed may be measured by subtracting the pressure difference between the outlet of the first bed and the outlet of the second bed from the pressure difference between the inlet of the first bed and the outlet of the second bed.

In one embodiment of the present invention, an overall pressure-drop is measured for the whole reactor and/or the adsorption unit. In another embodiment, a pressure-drop is measured across any one of the individual reactors and/or adsorption vessels in a multiple vessel reactor or a multiple-vessel adsorption unit. In another embodiment, a pressure-drop is measured across any one of the individual beds in a multiple-bed reactor or a multiple-bed adsorption unit. Multiple pressure-drop measurements across any one of the individual reactor vessels or beds may be performed.

The term "on-line" as used herein, means contacting the feedstock(s) with a solid particulate material in a reactor or an adsorption unit, e.g., catalyst or adsorbent, under conversion conditions. The term "on-line time" used herein, means the total on-line time, i.e., the total time when the solid particulate material in a reactor or an adsorption unit is in contact with the feedstock(s) under conversion conditions before the unit shutdown for regeneration or rejuvenation of the solid particulate material in the unit. For example, after contacting a fresh catalyst with a hydrocarbon feedstock for a period of time under catalytic conversion conditions, the unit needs to shutdown for catalyst regeneration. In this case, the "on-line time" is the sum of the time when the catalyst is in contact with a hydrocarbon feedstock under catalytic conversion conditions before unit shutdown for catalyst regeneration.

The "solid particulate material" as used herein, means a solid phase material in the reactor/adsorption vessel(s), bed(s), or tray(s) useful for the desired hydrocarbon conversion. In one embodiment of the present invention, the solid particulate material comprises at least one of a catalyst, an adsorbent, or any combination thereof. In another embodiment of the present invention, the solid particulate material comprises a plurality of compositions. Examples of catalytic solid particulate materials include metals, non-metals, metal compounds (e.g., oxides, chlorides, such as silica, silica-alumina, titanium oxide, aluminum chloride), solid acidic materials (e.g., zinc chloride, $BF_3$ on active carbon), solid basic materials (e.g., zinc oxide), macroporous solid particulate materials (with a pore size 500 Å and higher), mesoporous solid particulate materials (pore size ranged from 20 Å to 500 Å), microporous materials (pore size of 2 Å to 20 Å), or any combination thereof.

In one embodiment of the present invention, the solid particulate material comprises at least one of a catalyst, an adsorbent, or any combination thereof. In another embodiment of the present invention, the solid particulate material comprises a plurality of compositions. In another embodiment of the present invention, the solid particulate material comprises a molecular sieve.

The solid particulate material may also include at least one hydrogenation/dehydrogenation and/or at least one oxidative/reductive metal. Reference to the hydrogenation/dehydrogenation and/or oxidative/reductive metal or metals is intended to encompass such metal or metals in the elemental state (i.e. zero valent) or in some other catalytically active form such as an oxide, sulfide, halide, carboxylate and the like. Such metals are known to persons skilled in the art and include, for example, one or more metals, and metals of Groups IIIA, IVA, VA, VIA, VIIA, VIII, IB, IIB, IIIB, IVB, VB, VIB, and VIIB of the Periodic Table of the Elements. Examples of suitable metals include Group VIII metals (i.e., Pt. Pd, Ir, Rh, Os, Ru, Ni, Co and Fe), Group IVA metals (i.e., Sn and Pb), Group VA metals (i.e., Sb and Bi), and Group VIIB metals (i.e., Mn, Tc and Re). Noble metals (i.e., Pt, Pd, Ir, Rh, Os and Ru) are sometimes preferred.

The amount of metal present in the solid particulate material will be an "effective amount", that is, an amount sufficient to achieve the desired reaction, based on the total weight of the solid particulate material, which will generally be from about 0.001 to about 20 wt. % and, preferably 0.05 to 3.0 wt. %. The amount will vary with the nature of the metal and the nature of the process.

In another embodiment of the present invention, the solid particulate material comprises a porous material, which is characterized by a large specific surface area in pores and is used in a large number of applications of considerable commercial importance. The terms "porous solid particulate material" and "porous particulate material", as used herein, includes macroporous particulate material, mesoporous particulate material, microporous particulate material, and mixtures or combinations thereof.

In most applications that use porous particulate material, the fact that the phase interface between the porous particulate material and the medium (liquid or gas) in which such use occurs is large can be very important. Heterogeneous phase catalysts used in refinery processes, petrochemical conversion processes, and different environmentally related applications often comprise a use of porous particulate material, especially microporous particulate materials. Adsorbents for the selective adsorption in the gas or liquid phase or the selective separation of ionic compounds are often porous particulate material. In addition to these applications, porous particulate materials have recently become increasingly utilized in a number of more technologically advanced areas. Examples of such uses include use in chemical sensors, in fuel cells and batteries, in membranes for separation or catalytic purposes, in chromatography for preparative or analytical purposes, in electronics and optics, and in the production of different types of composites.

Although a large phase interface is often a fundamental requirement for use of porous particulate materials in different applications, a number of additional requirements related to the specific area of application are imposed on these materials. For example, the large phase interface available in the pores of the porous particulate material must be accessible and useable. Therefore, the porosity, pore size and pore size distribution in large pores(meso- and macropores) are often of major significance, especially when mass transport affects process performance. The surface properties of the porous particulate material can also be very important for the performance of the material in a given application. In this context, the purity of the material comprising the macrostructure is also significant.

Mesoporous particulate materials include amorphous metal oxide (non-crystalline) materials, which have mesoporous and, optionally, partially microporous structure. The pore size of the mesoporous particulate material is usually in the range of from about 20 Å to about 500 Å.

Microporous particulate materials include crystalline molecular sieves. Molecular sieves are characterized by the fact that they are microporous particulate materials with pores of a well-defined size ranging discretely from about 2 Å to about 20 Å. Most molecules, whether in the gas or liquid phase, both solid and organic, have dimensions that fall within this range at room temperature. Selecting a molecular sieve composition with a suitable and discrete pore size therefore allows separation of specific molecules from a mixture with other molecules of a different size through selective adsorption, hence the name "molecular sieve". Apart from the selective adsorption and selective separation of uncharged molecular sieve particles, the well-defined and discrete pore system of a molecular sieve enables selective ion exchange of charged particles and selective catalysis. In the latter two cases, significant properties other than the micropore structure include, for instance, ion exchange capacity, specific surface area and acidity.

Molecular sieves can be classified into various categories such as by their chemical composition and their structural properties. A group of molecular sieves of commercial interest is the group comprising the zeolites, which are defined as crystalline aluminosilicates. Another group is that of the metal silicates, structurally analogous to zeolites, but for the fact that they are substantially free of aluminum (or contain only very small amounts thereof). Still another group of molecular sieves are AlPO-based molecular sieves which contain framework tetrahedral units of alumina ($AlO_2$) and phosphorous oxide ($PO_2$) and, optionally, silica ($SiO_2$). Examples of such molecular sieves include SAPO, AlPO, MeAPO, MeAPSO, ELAPO, and ELAPSO.

A summary of existing technology, in terms of production, modification and characterization of molecular sieves, is described in the book "Zeolite Molecular Sieves—Structure, Chemistry, and Use"; Donald W. Breck, Robert E. Krieger Publishing Company, Malabar, Fla., 1984). In addition to molecular sieves, amorphous materials, chiefly silica, aluminum silicate and aluminum oxide, have been used as adsorbents and catalyst supports. A number of long-known techniques, such as spray drying, prilling, pelletizing and extrusion, have been and are being used to produce macrostructures in the form of, for example, spherical particles, extrudates, pellets and tablets of both micropores and other types of porous materials for use in catalysis, adsorption and ion exchange. A summary of these techniques is described in "Catalyst Manufacture," A. B. Stiles and T. A. Koch, Marcel Dekker, New York, 1995.

Molecular sieves/zeolites that find application in the present invention include any of the naturally occurring or synthetic crystalline molecular sieves. Examples of these zeolites include large pore zeolites, intermediate pore size zeolites, and small pore zeolites. These zeolites and their isotypes are described in "Atlas of Zeolite Structure Types", Eds. W. H. Meier, D. H. Olson and Ch. Baerlocher, Elsevier, Fourth Edition, 1996, which is hereby incorporated by reference. A large pore zeolite generally has a pore size of at least about 7 Å and includes LTL, VFI, MAZ, MEI, FAU, EMT, OFF, *BEA, and MOR structure type zeolites (IUPAC Commission of Zeolite Nomenclature). Examples of large pore zeolites include mazzite, offretite, zeolite L, VPI-5, zeolite Y, zeolite X, omega, Beta, ZSM-3, ZSM-4, ZSM-18, ZSM-20, SAPO-37, and MCM-22. An intermediate pore size zeolite generally has a pore size from about 5 Å to about 7 Å and includes, for example, MFI, MEL, MTW, EUO, MTT, MFS, AEL, AFO, HEU, FER, and TON structure type zeolites (IUPAC Commission of Zeolite Nomenclature). Examples of intermediate pore size zeolites include ZSM-5, ZSM-11, ZSM-12, ZSM-22, ZSM-23, ZSM-34, ZSM-35, ZSM-385, ZSM-48, ZSM-50, ZSM-57, silicalite 1, and silicalite 2. A small pore size zeolite has a pore size from about 3 Å to about 5.0 Å and includes, for example, CHA, ERI, KFI, LEV, SOD, and LTA structure type zeolites (IUPAC Commission of Zeolite Nomenclature). Examples of small pore zeolites include ZK-4, ZSM-2, SAPO-34, SAPO-35, ZK-14, SAPO-42, ZK-21, ZK-22, ZK-5, ZK-20, zeolite A, hydroxysodalite, erionite, chabazite, zeolite T, gmelinite, ALPO-17, and clinoptilolite.

In another embodiment, the process is an adsorption process having conversion conditions or adsorption conditions of a temperature from about 30° C. to about 350° C., a pressure from about 10 to about 7000 kPa-a, and a weight hourly space velocity from about 0.08 to about 2,000 $hr^{-1}$. In another embodiment, the process is a catalytic reaction process having conversion conditions of a temperature from about 50° C. to about 950° C., a pressure from about 10 to about 20000 kPa-a, and a weight hourly space velocity from about 0.08 to about 2,000 $hr^{-1}$.

In one embodiment, the process of the present invention comprises at least one of a catalytic cracking process, a transalkylation process, an isomerization process, a dewaxing process, an alkylation process, a hydrocarcking process, a reforming process, a light paraffins to olefins and/or aromatics process, an aromatic adsorption process, a toluene disproportionation process, an oligomerization process, an oxygenate to olefins and/or aromatics process, or any combination thereof.

The process of the present invention finds particular application in the adsorption process. The adsorption process involves contacting a mixture of hydrocarbons, existing either as a gas, liquid or mixed phase, with an adsorbent such as a molecular sieve for sufficient time to selectively adsorb the preferred hydrocarbon within the internal pore structure of the molecular sieve. The components of the mixture that are not adsorbed may be converted to absorbable hydrocarbons with a catalyst under conditions suitable for such a conversion. The hydrocarbons adsorbed are thereafter recovered from the internal pore structure of the molecular sieve by conventional desorption techniques. A portion of the adsorbent may be removed from the adsorption unit without interrupting the on-going adsorption process.

The adsorption process typically comprises multiple adsorbent beds, which are loaded with adsorbent in particulate form. Each adsorbent bed may comprise multiple trays/distributors. The adsorbent beds and trays/distributors may be located in a single adsorption vessel or operatively connected multiple vessels. The adsorption process is designed with an operating range of pressure-drop across the adsorbent vessel(s) or individual adsorbent bed(s). As the adsorption process comes on-line for production, the pressure-drop across the adsorbent vessel or adsorbent bed may increase after a period of time. The pressure-drop increase adversely impacts both operation and performance of the adsorption process.

It is not intended to be limited by any theory, however, the pressure-drop increase across the adsorbent vessel or adsorbent bed is believed to be a result of deposition of coke and other impurities (e.g., heavy metals in the feed) on the adsorbent, and the development of fines (e.g., crushed adsorbent/catalyst particulate material) formed after the adsorbent is exposed to the feedstock for a period of time. The formation of fines and/or the deposition of coke and other impurities on the adsorbent block a portion of the adsorption bed, which creates extra pressure-drop across the adsorbent bed or vessel. The present invention provides a method for mitigating the adverse effect of the pressure-drop increase without shutting down the process.

In one embodiment of the present invention, a portion of the solid particulate material is removed on-line under conversion conditions. The portion of the solid particulate material removed is such that it is sufficient to reduce the pressure-drop across the reactor vessel(s) or adsorbent bed to a pre-set pressure-drop based on the nature of the reaction or adsorption process.

The present invention finds application for selectively separating aromatic hydrocarbons, e.g., alkyl substituted benzenes. An example of such a separation is $C_8$ isomer, e.g., para-xylene, separation. During the separation process, i.e., adsorption, the alkyl substituted benzenes, e.g., meta-xylene and/or ortho-xylene, may be separated from other isomers, e.g., para-xylene.

The selective aromatic adsorption process involves contacting a feedstock containing the aromatic hydrocarbons, existing either as a gas, liquid or mixed phase, with a solid particulate material comprising at least one molecular sieve for sufficient time to selectively adsorb at least one aromatic hydrocarbon, e.g., alkyl substituted benzene. The unabsorbed components may be converted to absorbable isomers during contact with a solid particulate material including the molecular sieve. The alkyl substituted benzene absorbed is thereafter recovered by conventional desorption techniques. The temperature at which the adsorption process is conducted is not considered critical, so long as it is maintained below the desorption temperature of the adsorbed component. Preferably, the process is conducted at a temperature between about 40° C. and about 250° C.

The present invention finds application in the Parex™ process. The Parex™ process is a process for separation of para-xylene from $C_8$ aromatic isomers. The adsorbent is arranged as a succession of fixed beds with provision for the distribution and collection of the inlet and outlet streams of hydrocarbon between each of several beds of adsorbent. These streams are distributed through a rotary valve. A summary of the Parex™ process is described in "Handbook of Petroleum Refining Processes," R. A. Myers, McGraw-Hill, New York, 1986, which is hereby incorporated by the references. The operating temperature of the Parex™ process is defined at 30° C. to about 350° C. and preferably within the range of about 40° C. to about 250° C. The operating pressure of the Parex™ process is defined from about 100 to about 4300 kPa-a and preferably in the range of about 100 to about 3000 kPa-a. A typical Parex™ process adsorbent comprises a molecular sieve with a zeolite structure referred to as the crystalline aluminosilicate zeolites and can comprise both the natural and synthetic aluminosilicates. The conditions and adsorbents are described in U.S. Pat. No. 3,686,342, which is incorporated herein by reference.

The process of the present invention finds particular application in a reactive distillation process. A reactive distillation process is preferably carried out in a reaction/distillation column. In this embodiment, the hydrocarbons to undergo conversion are usually fed continuously to the reaction/distillation column and the resulting product is continuously withdrawn from the top and/or bottom of the reaction/distillation column. In this embodiment, the continuous removal of the desired product from the reaction/distillation column increases the extent of reaction achieved within the column, thus providing very high conversion along with low by-product formation. Equipment suitable for carrying out reactive distillation is disclosed in PCT Publication No. WO 99/38823, which is hereby incorporated by reference.

The present invention also finds particular application in a process for isomerizing one or more xylene isomers in a $C_8$ aromatic feed to obtain ortho-, meta-, and para-xylene in a ratio approaching the equilibrium value. In particular, xylene isomerization is used in conjunction with a separation process to manufacture para-xylene. For example, a portion of the para-xylene in a mixed $C_8$ aromatic stream may be recovered using processes known in the art, e.g., crystallization, adsorption, etc. The resulting stream is then reacted under xylene isomerization conditions to restore ortho-, meta-, and para-xylenes to a near equilibrium ratio. Ethylbenzene in the feed is either removed from the stream or is converted during the process to xylenes or to benzene, which are easily separated by distillation. The isomerate is blended with fresh feed and the combined stream is distilled to remove heavy and light by-products. The resultant $C_8$ aromatic stream is then recycled to repeat the cycle.

In the vapor phase, suitable isomerization conditions include a temperature in the range 250° C.-600° C., preferably 300° C.-550° C., a pressure in the range 10-5000 kPa-a, preferably 1000-2500 kPa-a, and a weight hourly space velocity (WHSV) of 0.1 to 100 $h^{-1}$, preferably 0.5 to 50 $h^{-1}$. Optionally, isomerization in the vapor phase is conducted in the presence of 0.1 to 30.0 moles of hydrogen per mole of alkylbenzene.

The xylene isomerization reaction is usually carried out in a fixed bed reactor containing a catalyst. The xylene isomerization reaction can also be carried out in sequential beds using two catalysts. In this embodiment, each catalyst is in a separate bed or one of the catalysts forms one part of a bed while the second catalyst forms the remaining part of the bed and is located downstream with respect to the first catalyst. The first catalyst is used primarily for ethylbenzene conversion while the second catalyst is used primarily for xylene isomerization.

When used to isomerize feeds containing ethylbenzene, the catalyst will preferably contain at least one hydrogenation metal.

The process of the present invention finds particular application in the transalkylation of polyalkylaromatic compounds. The feed used in the process will usually comprise one or more aromatic compounds containing at least 9 carbon atoms such as mesitylene (1,3,5-trimethylbenzene), durene (1,2,4,5-tetramethylbenzene), hemimellitene (1,3,3-trimethylbenzene), pseudocumene (1,2,4-trimethylbenzene), prehnitene (1,2,3,4-trimethylbenzene), isodurene (1,2,3,4-tetramethylbenzene), and 1,3,5-triethylbenzene. The feed can also be one containing multi-alkyl-aromatics, e.g., pentamethyl-benzene with naphthalene/methyl naphthatene. Preferably, the catalyst is combined with a hydrogenation component, such as platinum, palladium or rhenium, and is used in the catalytic conversion of $C_{9+}$ alkylaromatic compounds, either alone or in the presence of toluene and/or benzene, to produce xylenes. Such conversion is typically effected at a temperature of from about 340° C. to about 510° C., and preferably from about 400° C. to about 450° C., a pressure of from about 800 to about 4000 kPa-a, and preferably from about 1500 to about 3500 kPa-a, a weight hourly space velocity (WHSV) of between about 0.1 and about 200 $hr^{-1}$, and preferably between about 0.5 and about 20 $hr^{-1}$, and a hydrogen, $H_2$, to hydrocarbon, HC, molar ratio of between about 1 and about 5, and preferably from about 1 to about 3.

In another aspect of any of the above embodiments, the process of the present invention comprises at least one of a continuous process, a batch process, or any combination thereof. In one embodiment of the present invention, the process comprises at least one of an adsorption process, a selective toluene disproportionation process, a toluene disproportionation process, a reforming process, an ethylbenzene isomerization process, an aromatic alkylation process, a methanol to aromatics process, a methane to aromatics process, an aromatic alkylation process, an aromatic transalkylation process, a xylene isomerization process, a catalytic cracking process, or any combination thereof.

In one embodiment, the present invention comprise at least one removing step to remove at least 0.1 wt. % of the solid particulate material in the reactor or the adsorption unit under the conversion conditions while the feedstock is flowing through the reactor or adsorption unit. The removing step is performed for less than 95% of the on-line time.

The removal of the solid particulate material may be carried out in any conventional way. The removing step of this invention is performed under the conversion conditions while the solid particulate material is on-line, i.e., in contact with a hydrocarbon feedstock. In one embodiment of this invention, the removing step comprises installation of a nozzle or a plurality of nozzles on the reactor and/or adsorption vessels with valve(s). The nozzles may be located at different locations of a reactor and/or adsorption vessel, bed, or tray. By opening the valve for a period of time, a portion of the solid particulate material may be removed from the reactor and/or adsorption vessel, bed, or tray, due to gravity, pressure difference, or the combination of gravity and pressure difference. The solid particulate material may also be removed mechanically. In one embodiment, the solid particulate material may be removed together with a portion of the hydrocarbon feedstock inside the reactor and/or adsorption vessel, bed, or tray. In another embodiment, the portion of the hydrocarbon feedstock removed together with the solid particulate material may be separated from the solid particulate material for further processing, e.g., recycle back to the reactor and/or adsorption unit. In a preferred embodiment, the removing step is carried out under an inert environment, such as, inert blanket with nitrogen, hydrogen, and/or helium.

In another embodiment, the present invention comprises an apparatus useful for on-line solid particulate material removal. The apparatus comprises a drum equipped with a filter or screen separating the drum into a first portion and a second portion. The drum also is equipped with at least two nozzles, wherein a first nozzle is attached to the first portion of the drum and a second nozzle is attached to the second portion of the drum. The first nozzle is further connected by pipe and at least one valve to any one of the removing locations on the reactor and/or the adsorption vessel. To remove catalyst or adsorbent from the reactor and/or adsorption vessel, open the valve and let the solid particulate material and/or the hydrocarbon feedstock flow out of the reactor and/or adsorption vessel (driven by pressure or gravity) into the drum. The hydrocarbon feedstock passes through the filter (e.g., a screen) in the drum and is returned to the reactor and/or adsorption vessel through the second nozzle. The solid particulate material is retained by the screen and remains in the drum. When sufficient solids have been removed, the nozzle valve is closed and the drum and adsorbent is cleared of hydrocarbon. The drum may further comprise a third nozzle attached to the first portion of the drum, preferably right above the filter/screen. The solids may be removed from the drum through the third nozzle. Preferable, the drum may further comprise a fourth nozzle attached the first portion of the drum with an inert gas source, e.g., nitrogen, to provide an inert gas blanket. More preferable, the drum may further comprise a fifth nozzle attached to the second portion of the drum to release the inert gas. Even more preferable, the drum may further comprise a site glass suitable to observe the amount of solid particulate material removed. This process is repeated for each removing location and for each removing step.

In one aspect of any of the above embodiments, the fractional time for any removing step is less than 90% of the on-line time, preferably less than 75% of the on-line time, even more preferably less than 50% of the on-line time, even more preferably less than 25% of the on-line time, even more preferably less than 10% of the on-line time, and most preferably less than 5% of the on-line time.

In another embodiment, the present invention further comprises a plurality of removing steps for a cumulative fractional time less than 90% of the on-line time, preferably less than 75% of the on-line time, even more preferably less than 50% of the on-line time, even more preferably less than 25% of the on-line time, even more preferably less than 10% of the on-line time, and most preferably less than 5% of the on-line time.

In yet another embodiment of the present invention, the process further comprises removing the solid particulate material at a plurality of locations in the reactor or adsorption unit. In yet another embodiment of the present invention, the process further comprises removing the solid particulate material at a plurality of locations in the vessel(s) or bed(s). For example, three removing nozzles may be installed at the top, middle, and the bottom of a reactor bed, which enables the removal of catalyst separately or simultaneously from three locations. In another example, two removing nozzles may be installed with one close to the center of the catalyst bed and another one close to the wall of the reactor. This configuration enables separately or simultaneously removing catalyst from both locations.

In one embodiment of the present invention, the portion of the solid particulate material removed is less than 95 wt. %, preferably, less than 50 wt. %, more preferably, less than 20 wt. % of the total solid particulate material in the reactor system or the adsorption unit. The "total solid particulate material in the reactor system or the adsorption unit" means all solid particulate material, e.g., catalyst or adsorbent in the reactor system or the adsorption unit. For example, the total solid particulate material in a multiple bed adsorption unit is the sum of all adsorbent in all adsorption beds. In another aspect of any of the above embodiments, the portion of the solid particulate material removed is more than 0.1 wt. %, preferably more than 0.5 wt. %, more preferably more than 1 wt. %, even more preferably more than 5 wt. %, most preferably more than 10 wt. % of the solid particulate material in the reactor or adsorption unit.

In another embodiment, the present invention further comprises a step of replacing at least 0.1 wt. %, preferably at least 1 wt. %, more preferably at least 50 wt. %, even more preferably at least 90 wt. %, most preferably 100 wt. % of the removed solid particulate material with a fresh, a regenerated, or a rejuvenated solid particulate material to the reactor on-line under the conversion conditions. The fresh, the regenerated, or the rejuvenated solid particulate material may be added using the same removing locations. In one embodiment, the fresh, the regenerated, or the rejuvenated solid particulate material is loaded to the top of the reaction vessel(s) or adsorption vessel(s). In another embodiment, the fresh, the regenerated, or the rejuvenated solid particulate material may be added to any of the reactor/adsorption bed or tray on-line under hydrocarbon conversion conditions. In another aspect of any of the above embodiments, the present invention further comprises a plurality of loading steps.

The catalyst and/or adsorbent may be regenerated under regeneration conditions. In one embodiment of the present invention, the catalyst and/or adsorbent is regenerated under regenerating conditions comprising a temperature range of about 30 to 900° C., a pressure range of about 10 to 20000 kPa-a, wherein the regenerating conditions comprise a feed having an oxidative reagent.

The catalyst and/or adsorbent may be rejuvenated under rejuvenation conditions. In another embodiment of the present invention, the catalyst and/or adsorbent is rejuvenated under rejuvenating conditions comprising a temperature range of about 30° C. to about 900° C., a pressure range of about 10 to 20000 kPa-a, wherein the rejuvenating conditions comprise a feed having a reductive reagent.

After removing or loading the solid particulate material (catalyst/adsorbent) from the reactor/adsorption unit, the packing of the solid particulate material (catalyst/adsorbent) inside the reactor/adsorption unit may be disturbed, which may impact some performance parameters. In one aspect of any of the above embodiments, the process may further comprise a step of redistributing the solid particulate material remaining in the reactor and/or the adsorption unit. It is well known to anyone skilled in the art that a catalyst/adsorbent redistribution will improve catalyst uniformity in a reactor and/or adsorption unit after loading of new catalyst/adsorbent bed and/or disturbing of the catalyst/adsorbent bed due to any operational upset. The redistributing step may be performed by any convenient way, such as, catalyst/adsorption bed fluidization. For example, the catalyst/adsorption bed may be fluidized by flowing inert gas or liquid hydrocarbons (such as feedstock or product) from bottom of the catalyst/adsorption bed at a sufficient velocity to fluidize the solid particulate material (catalyst/adsorbent). Fluidization, or fluidizing, converts a bed of solid particles into an expanded, suspended mass that has many properties of a liquid. Fluidized beds are used successfully in a multitude of processes both catalytic and noncatalytic. A summary of the fluidization and fluidized bed design is described in "Perry's Chemical Engineers' Handbook", Eds. R. H. Perry, D. W. Green and J. O. Maloney, McGraw-Hill Book Company, Sixth Edition, 1984, which is hereby incorporated by reference. The redistributing step may also be performed by a backflushing step, which is well known for increasing efficiency and uptime of a plant. The backflushing filter is commercially available from RPA Process Technologies (Portage, Mich. USA).

In one embodiment, the redistributing step is performed within one year from the removing and/or loading step, preferably within one month from the removing and/or loading step, and more preferably within two weeks from the removing and/or loading step. In another embodiment, the redistributing step is performed within one day from the removing and/or loading step. The time between the redistributing step and the removing and/or loading step depends on the nature of the catalytic process or the adsorption process. For example, the performance of a selective toluene disproportionation process or a selective adsorption process is highly sensitive to the uniformity of the catalyst bed. It is preferred to perform the redistributing step within two weeks or even a day to avoid performance debit. The performance of the catalytic and/or adsorption process may be improved by performing the redistributing step after the removing and/or loading step. It is not intended to be limited by any theory, however, it is believed that the performance improvement of the catalytic and/or adsorption process after performing the redistributing step is at least partially due to the improved uniformity of the catalytic and/or adsorbent bed.

In one aspect of any of the above embodiments, the present invention further comprises a step of monitoring the pressure-drop across at least a portion of the reactor and/or adsorbent vessel(s) or bed(s). In one embodiment of the present invention, the removing step is initiated when the pressure-drop is above a pre-set pressure-drop upper limit of the reaction and/or adsorption conditions. In another embodiment of the present invention, the removing step is sufficient to reduce the pressure-drop to a point within the pre-set pressure-drop range of the reaction and/or adsorption conditions. The upper limit or the pre-set pressure-drop range of a reactor or an adsorption unit is determined by the nature of the hydrocarbon conversion, the construction material of reactor and/or adsorption vessel(s), the equipment for providing pressure head, e.g., feed pumps, and upstream and/or downstream limitations.

The loading step may be done by reversing the above mentioned removing operation. A portion of the adsorbent/catalyst is put into the drum above the filter. A pressurized fluid is fed through the second nozzle to sweep the solids into the reactor and/or adsorption vessel. The first nozzle may be connected to any one of the removing locations of the reactor and/or adsorption vessel or a new loading location of the reactor and/or adsorption vessel, e.g., the location on the top of the reactor and/or adsorption vessel.

In a preferred embodiment of this invention, the feed rate for the feedstock is at least 10 kg per day.

The following examples illustrate exemplary preferred embodiments:

EXAMPLE 1

The following example is a computer simulation of a 5.47 meter long catalytic reactor with an initial pressure-drop across the catalyst bed of 172 kPa and a catalyst packing void space of 0.35. The void space is the ratio of the volume available for liquid/gas flow in a solid particulate material packed reactor/adsorption bed over the total volume of the reactor/adsorption bed. A decrease of the void space is an indication that the catalyst bed is plugged by fines or coke after being contacted with feedstock. The pressure-drop change due the plugging is calculated by the Ergun equation, which is described in "Fluid Flow through Packed Columns", Chem. Eng. Prog. 48: 89-94, February 1952, S. Ergun, which is hereby incorporated by reference. The results of the simulation are shown in Table 1.

TABLE 1

| | Cases | | | |
|---|---|---|---|---|
| | 1 | 2 | 3 | 4 |
| Pressure-Drop (kPa) | 172 | 189 | 217 | 276 |
| Void Space | 0.35 | 0.34 | 0.33 | 0.32 |
| Void Space Change (%) | | −2% | −5% | −10% |
| Pressure-Drop after Selectively Removing 50% plugging with 0.5 wt. % catalyst removed (kPa) (Pressure-Drop Change (%)) | 171 (0.5) | 180 (4.8) | 193 (11.1) | 217 (21.4) |
| Pressure-Drop after Selectively Removing 80% plugging with 0.5 wt. % catalyst removed (kPa) (Pressure-Drop Change (%)) | 171 (0.5) | 175 (7.4) | 180 (17.1) | 189 (31.5) |
| Pressure-Drop after Selectively Removing 90% plugging with 0.5 wt. % catalyst removed (kPa) (Pressure-Drop Change (%)) | 171 (0.5) | 174 (7.9) | 176 (18.9) | 180 (34.8) |

As shown in Table 1, case 1 is a simulation representing a fresh catalyst loading where there is no void space plugging. The decrease of pressure-drop after removing 0.5 wt. % of catalyst is proportional to the amount of the catalyst removed. Cases 2, 3, and 4 are simulations representing the pressure-drop changes after 2%, 5%, and 10% void space plugging, wherein the pressure-drops across the adsorption unit are 189, 217, and 276 kPa correspondingly. The selectively removing of the plugging, such as by selective removed the top layer of the adsorbent bed, substantially reduces pressure-drop across the reactor.

EXAMPLE 2

The following example is a computer simulation of a 1.5 meter long adsorbent bed of an adsorption unit with an initial pressure-drop across the adsorbent bed of 27.58 kPa and an adsorbent packing void space of 0.30. The pressure-drop change due the plugging is calculated by the Ergun equation. The results of the simulation are shown in table 2.

TABLE 2

| | Cases | | | |
|---|---|---|---|---|
| | 5 | 6 | 7 | 8 |
| Pressure-Drop (kPa) | 27.58 | 30.06 | 34.28 | 42.91 |
| Void Space | 0.30 | 0.29 | 0.29 | 0.27 |
| Void Space Change (%) | | −2% | −5% | −10% |
| Pressure-Drop after Selectively Removing 50% plugging with 0.5 wt. % catalyst removed (kPa) (Pressure-Drop Change (%)) | 27.44 (0.5) | 28.79 (4.2) | 30.72 (10.4) | 34.28 (20.1) |
| Pressure-Drop after Selectively Removing 80% plugging with 0.5 wt. % catalyst removed (kPa) (Pressure-Drop Change (%)) | 27.44 (0.5) | 28.06 (6.7) | 28.79 (16.0) | 30.06 (30.0) |
| Pressure-Drop after Selectively Removing 90% plugging with 0.5 wt. % catalyst removed (kPa) (Pressure-Drop Change (%)) | 27.44 (0.5) | 27.82 (7.5) | 28.18 (17.8) | 28.79 (32.9) |

As shown in Table 2, case 5 is a simulation representing a fresh adsorbent loading where there is no void space plugging. The decrease of pressure-drop after removing 0.5 wt. % of adsorbent is proportional to the amount of the adsorbent removed. Cases 6, 7, and 8 are simulations representing the pressure-drop changes after 2%, 5%, and 10% void space plugging, wherein the pressure-drops across the adsorption unit are 30.06, 34.28, and 42.91 kPa correspondingly. The selective removal of the plugging, such as by selectively removing the top layer of the adsorbent bed, substantially reduces pressure-drop across the adsorption unit.

All patents, patent applications, test procedures, priority documents, articles, publications, manuals, and other documents cited herein are fully incorporated by reference to the extent such disclosure is not inconsistent with the present invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

We claim:

1. A process for selective para-xylene adsorption comprising the steps of:
   A) feeding a feedstock containing para-xylene to an adsorption unit;
   B) adsorbing said feedstock in said adsorption unit with a solid particulate adsorbent useful for adsorbing at least one component from said feedstock under adsorption conditions;
   C) withdrawing adsorbed feedstock from said adsorption unit;
   D) desorbing said adsorbed component from said solid particulate adsorbent; and
   E) removing, under said adsorption conditions, at least a portion of said solid particulate adsorbent while said feedstock is being fed to said adsorption unit, wherein said portion is more than 0.1 wt. % of said solid particulate adsorbent in said adsorption unit and wherein said solid particulate adsorbent removal occurs during a fraction of the time of step (B), said fraction being less than about 95% of the time of step (B) wherein said step (E) further comprises removing said solid particulate adsorbent from a plurality of locations in said adsorption unit.

2. The process recited in claim 1, further comprising a step of adding at least 0.1 wt. % of fresh solid particulate adsorbent, regenerated solid particulate adsorbent, rejuvenated solid particulate adsorbent, or any combination thereof, to said adsorption unit under said adsorption conditions after step (E).

3. The process recited in claim 2, further comprising a step of redistributing the remaining and added solid particulate adsorbent in said adsorption unit.

4. The process recited in claim 3, wherein said redistributing step is performed less than one month after said removing step.

5. The process recited in claim 3, wherein said redistributing step is performed less than two weeks after said removing step.

6. The process recited in claim 3, wherein said redistributing step is performed less than one day after said removing step.

7. The process recited in claim 1, wherein said adsorption unit has a plurality of adsorption/desorption beds.

8. The process recited in claim 3, wherein said step (E) further comprises removing said solid particulate adsorbent from at least one location in any one of said adsorption/desorption beds.

9. The process recited in claim 2, further comprising a step of regenerating the removed adsorbent under regenerating conditions comprising a temperature in the range of about 30 to 900° C., a pressure in the range of about 10 to 7000 kPa-a, wherein said regenerating conditions comprise a feed having an oxidative reagent.

10. The process recited in claim 2, further comprising a step of rejuvenating the removed adsorbent under rejuvenating conditions comprising a temperature in the range of about 30 to 900° C., a pressure in the range of about 10 to 7000 kPa-a, wherein said rejuvenating conditions comprise a feed having a reductive reagent.

11. The process recited in claim 1, wherein said fraction is less than 50% of the time of step (B).

12. The process recited in claim 1, wherein said fraction is less than 20% of the time of step (B).

13. The process recited in claim 1, wherein said fraction is less than 10% of the time of step (B).

14. The process recited in claim 1, wherein said fraction is less than 5% of the time of step (B).

15. The process recited in claim 1, wherein said portion is more than 0.3 wt. % of said adsorbent in said adsorption unit.

16. The process recited in claim 1, wherein said portion is more than 1wt. % of said adsorbent in said adsorption unit.

17. The process recited in claim 1, wherein said portion is more than 5 wt. % of said adsorbent in said adsorption unit.

18. The process recited in claim 1, wherein said adsorbent comprises a molecular sieve.

19. The process recited in claim 1, wherein said feedstock further comprises meta-xylene, ortho-xylene, or ethylbenzene.

20. The process recited in claim 1, wherein said feedstock further comprises hydrogen.

21. The process recited in claim 1, wherein said selective para-xylene adsorption is Parex™.

22. The process recited in claim 1, wherein the feed rate of said feedstock is at least 10 kg per day.

23. The process recited in claim 1, further comprising a step of monitoring the pressure-drop across at least a portion of said adsorption unit.

24. The process recited in claim 23, wherein said removing step is initiated when said pressure-drop is above a pre-set pressure-drop upper limit.

25. The process recited in claim 24, wherein said removing step is continued at least until said pressure-drop is below said pre-set pressure-drop upper limit.

26. The process recited in claim 1, wherein said adsorption unit comprises a fixed bed adsorption unit, a fluidized bed adsorption unit, a rising-bed adsorption unit, or any combination thereof.

27. A process for selective para-xylene adsorption comprising the steps of:
   A) feeding a feedstock containing para-xylene to an adsorption unit;
   B) adsorbing said feedstock in said adsorption unit with a solid particulate adsorbent useful for adsorbing at least one component from said feedstock under adsorption conditions;
   C) withdrawing adsorbed feedstock from said adsorption unit;
   D) desorbing said adsorbed component from said solid particulate adsorbent;
   E) monitoring a pressure-drop across at least a portion of said adsorption unit;
   F) removing, under said adsorption conditions, at least a portion of said solid particulate adsorbent while said feedstock is being fed to said adsorption unit, said removing step is initiated when said pressure-drop is above a pre-set pressure-drop upper limit, and said removing step is continued at least until said pressure-drop is below said pre-set pressure-drop upper limit; and
   G) redistributing the remaining solid particulate adsorbent in said adsorption unit, wherein said portion is more than 0.1 wt. % of said solid particulate adsorbent in said adsorption unit, wherein said solid particulate adsorbent removal occurs during a fraction of the time of step (B), said fraction being less than about 95% of the time of step (B), wherein said selective para-xylene adsorption is Parex™, and wherein said redistributing step is performed less than one week after the removing step wherein said step (E) further comprises removing said solid particulate adsorbent from a plurality of locations in said adsorption unit.

28. The process recited in claim 27, further comprising a step of adding at least 0.1 wt. % of fresh solid particulate adsorbent, regenerated solid particulate adsorbent, rejuvenated solid particulate adsorbent, or any combination thereof, to said adsorption unit under said adsorption conditions after step (F).

29. The process of claim 1, wherein said process is an aromatics adsorption process.

* * * * *